United States Patent
Sakai et al.

(10) Patent No.: US 10,806,193 B2
(45) Date of Patent: Oct. 20, 2020

(54) SUPPORTER AND METHOD FOR MANUFACTURING SAME

(71) Applicant: TOSCOM CO., LTD., Nagano, Nagano (JP)

(72) Inventors: Kazuhito Sakai, Nagano (JP); Shun Kitahara, Nagano (JP)

(73) Assignee: TOSCOM CO., LTD., Nagano, Nagano (JP)

( * ) Notice: Subject to any disclaimer, the term of this patent is extended or adjusted under 35 U.S.C. 154(b) by 402 days.

(21) Appl. No.: 15/524,736

(22) PCT Filed: Nov. 6, 2015

(86) PCT No.: PCT/JP2015/081259
§ 371 (c)(1),
(2) Date: May 5, 2017

(87) PCT Pub. No.: WO2016/072482
PCT Pub. Date: May 12, 2016

(65) Prior Publication Data
US 2017/0318872 A1    Nov. 9, 2017

(30) Foreign Application Priority Data

Nov. 7, 2014  (JP) .................................. 2014-227493

(51) Int. Cl.
*A41D 13/06*  (2006.01)
*A61F 13/06*  (2006.01)
(Continued)

(52) U.S. Cl.
CPC ............ *A41D 13/065* (2013.01); *A41B 11/00* (2013.01); *A41B 11/02* (2013.01); *A41D 13/06* (2013.01);
(Continued)

(58) Field of Classification Search
CPC ...... A41D 13/065; A41D 13/06; A41D 13/08; A61F 5/0109; A61F 5/0118;
(Continued)

(56) References Cited

U.S. PATENT DOCUMENTS 3,322,873 A * 5/1967 Hitchcock .......... B29D 99/0064
264/222
4,292,263 A * 9/1981 Hanrahan ............ A41D 13/015
128/892
(Continued)

FOREIGN PATENT DOCUMENTS

JP       11-206947 A     8/1999
JP       3073408 U      11/2000
(Continued)

OTHER PUBLICATIONS

International Search Report, issued in PCT/JP2015/081259 (PCT/ISA/210), dated Jan. 26, 2016.

*Primary Examiner* — Jameson D Collier
(74) *Attorney, Agent, or Firm* — Birch, Stewart, Kolasch & Birch, LLP

(57) ABSTRACT

In the configuration of a supporter that at least partially includes a tubular cover portion which covers a part of a human body and which elastically expands and contracts, a load addition pattern portion that is adhered to at least a part of a half or more circumference in a circumferential direction on the front surface of the tubular cover portion and that can apply a load of a predetermined magnitude to the part of the human body when the part of the human body to which the tubular cover portion is fitted is moved is continuously formed of an elastic rubber material. Preferably, as the elastic rubber material, a silicone rubber material is used, and a part or the whole of the area of the load addition
(Continued)

pattern portion is formed with a mesh-shaped portion and preferably a honeycomb shape.

1 Claim, 10 Drawing Sheets

(51) Int. Cl.
    *A41B 11/02*     (2006.01)
    *A41D 19/015*     (2006.01)
    *A41B 11/00*     (2006.01)
    *A41D 19/04*     (2006.01)
    *A41D 13/08*     (2006.01)
    *A61F 13/10*     (2006.01)
    *A61F 13/00*     (2006.01)
    *A61F 5/01*     (2006.01)

(52) U.S. Cl.
    CPC ............ *A41D 13/08* (2013.01); *A41D 19/015* (2013.01); *A41D 19/04* (2013.01); *A61F 5/0109* (2013.01); *A61F 5/0111* (2013.01); *A61F 5/0118* (2013.01); *A61F 13/00008* (2013.01); *A61F 13/00034* (2013.01); *A61F 13/06* (2013.01); *A61F 13/10* (2013.01); *A41B 2500/52* (2013.01); *A41D 2500/52* (2013.01)

(58) Field of Classification Search
    CPC .................. A61F 5/0106; A61F 5/0123; A61F 13/00008; A61F 13/00034; A61F 13/101; A61F 13/00029; A61F 13/00038; A61F 13/061
    USPC ...... 2/1, 46, 22, 24, 59, 62, 455; 602/62, 63
    See application file for complete search history.

(56) References Cited

U.S. PATENT DOCUMENTS

| | | | | |
|---|---|---|---|---|
| 4,484,361 A * | 11/1984 | Leighton | ................ | A41D 13/08 2/16 |
| 4,700,698 A * | 10/1987 | Kleylein | ................ | A61F 13/062 602/26 |
| 4,796,303 A * | 1/1989 | Atwater | ................ | A41D 13/065 2/24 |
| 5,077,837 A * | 1/1992 | Meistrell | ............... | A41D 13/065 2/16 |
| 5,450,625 A * | 9/1995 | Hu | .................... | A41D 13/0568 2/16 |
| 5,924,140 A * | 7/1999 | Chi | .................... | A41D 13/0568 2/16 |
| 6,279,160 B1 * | 8/2001 | Chen | .................... | A41D 13/065 2/24 |
| 6,336,220 B1 * | 1/2002 | Sacks | .................... | A42B 3/065 2/22 |
| 7,273,464 B2 * | 9/2007 | Reinhardt | ............... | A61F 13/06 602/26 |
| 7,615,022 B2 * | 11/2009 | Nordt, III | ............ | A61F 5/0106 602/16 |
| 7,662,122 B2 * | 2/2010 | Sterling | ................ | A61F 5/0123 128/882 |
| 8,961,733 B2 * | 2/2015 | Dodd | ................ | A41D 13/0153 156/290 |
| 2003/0050586 A1 * | 3/2003 | Domanski | ............ | A61F 5/0109 602/21 |
| 2006/0107444 A1 * | 5/2006 | Huggins | ............... | A41B 11/004 2/239 |
| 2007/0021706 A1 * | 1/2007 | Braunstein | ........... | A61F 5/0109 602/63 |
| 2008/0256691 A1 * | 10/2008 | White | ................ | A41D 13/0015 2/455 |
| 2010/0031706 A1 * | 2/2010 | Chaveau | ............... | A41B 11/005 66/178 R |
| 2011/0209267 A1 * | 9/2011 | Rush | ........................ | A41D 1/08 2/228 |
| 2012/0277649 A1 * | 11/2012 | Matsuo | ................ | A41D 13/065 602/63 |
| 2013/0160189 A1 * | 6/2013 | Yang | .................. | A63B 21/0552 2/227 |
| 2013/0239299 A1 * | 9/2013 | Carter-Cohen | ......... | A45F 5/022 2/300 |
| 2014/0128785 A1 * | 5/2014 | Dickson | ............... | A41B 11/008 601/84 |
| 2014/0189926 A1 * | 7/2014 | Gudalis | .............. | A41D 13/0156 2/16 |
| 2014/0325729 A1 * | 11/2014 | Hsieh | .................... | A41D 13/065 2/16 |
| 2015/0101097 A1 * | 4/2015 | Clarke | ................. | A41D 13/065 2/24 |
| 2016/0059516 A1 * | 3/2016 | Harris | ....................... | B32B 7/12 442/1 |

FOREIGN PATENT DOCUMENTS

| | | | | |
|---|---|---|---|---|
| JP | 2003-52727 A | 2/2003 | | |
| JP | 2006-116252 A | 5/2006 | | |
| JP | 2006-118088 A | 5/2006 | | |
| JP | 2009-50418 A | 3/2009 | | |
| JP | 3160113 U | 6/2010 | | |
| JP | 2010-144287 A | 7/2010 | | |
| JP | 2012-34718 A | 2/2012 | | |
| JP | 3180174 U | 12/2012 | | |
| WO | WO-8800819 A1 * | 2/1988 | ........... | A61F 13/061 |
| WO | WO-9101704 A1 * | 2/1991 | | |
| WO | WO-2011125552 A1 * | 10/2011 | ........... | A61F 5/0109 |

\* cited by examiner (a)

(b)

(c)

SUPPORTER AND METHOD FOR MANUFACTURING SAME

TECHNICAL FIELD

The present invention relates to supporters which it least partially include a tubular cover portion that covers a pan of a human body and that elastically expands and contracts and methods of manufacturing such supporters.

BACKGROUND ART

Conventionally, supporters are known which are used by being fitted to a leg in order to protect an ankle joint, an Achilles' and the like, and as these types of supporters, a supporter for an ankle is disclosed in patent literature 1, a leg wear is disclosed in patent literature 2 and a supporter for an ankle joint is disclosed in patent literature 3.

The supporter for an ankle disclosed in patent literature 1 is intended to easily realize, only by being fitting to an ankle, a form of taping which is most suitable for an ankle and which is effective for improving or preventing an ankle joint disorder such as a pain in an anterior at the time of dorsiflexion of an ankle joint. Specifically, a supporter, is provided which has the following configuration. In a substantially center portion of a strip-shaped supporter body along its length in which a planar fastener bonding fiber layer is provided on the outer surface of a stretchable elastic rubbery sheet and which is formed of a base material, a width division tear is provided which can be extended to a length from a lower end of a malleolus on one side through a back surface of an Achilles' heel portion or a foot sole to a lower end of the malleolus on the other side, in each of both ends of the head and tail of the supporter body, a planar fastener body which is extended toward the back side and whose width is narrow is provided so as to be extended and furthermore, in a position which is displaced from the base end of the planar fastener body at the head portion of the supporter body an insertion hole is provided through which the planar fastener body at the tail portion of the supporter body is freely inserted.

The leg wear disclosed in patent literature 2 is intended such that the leg wear can sufficiently apply a force in a direction toward the outside with respect to a foot thumb and that the leg wear can easily be put on. Specifically, a leg wear is provided which has the following configuration. In a foot portion of a sock, a toe-side support organized with rubber threads is provided, a side support organized with rubber threads is provided from the toe-side support to a thumb portion and thus when the sock is worn, a force resulting from the return of the side support to a shape in a state where the sock is not worn acts on the side of a heel, with the result that by utilization of such a force, a pulling force toward the side of the heel is applied to the side surface of the thumb portion which holds the foot thumb of a wearer.

Furthermore, the supporter for an ankle joint disclosed in patent literature 3 is intended to provide a supporter for an ankle joint which can be securely fixed to an ankle. Specifically, a supporter for an ankle joint is provided which has the following configuration. On a lateral malleolus side of a substantially tubular supporter body which has a shape suitable for covering all ankle and a portion in the vicinity thereof in a state where they are stably in intimate contact with each other, fixed belts formed the shape of elongated strips are attached to the positions of different heights, the fixed belts are individually inserted through fixed belt insertion holes provided on a medial malleolus side of the supporter body from the inside toward the outside and by a portion of the fixed belt on the tip end side and a velvet-type fastener provided on a portion of the supporter body on the lateral malleolus side, the portion of the fixed belt on the tip end side can be fixed to a position of the supporter body on the lateral malleolus side when the fixed belt is folded to the lateral malleolus side.

CITATION LIST

Patent Literature

Patent Literature 1: Japanese Unexamined Patent Application Publication No. 2010-144287
Patent Literature 2: Japanese Unexamined Patent Application Publication No. 2012-34718
Patent Literature 3: Japanese Utility Model Registration No. 3073408

SUMMARY OF INVENTION

Technical Problem

However, the above-described conventional supporters disclosed in patent literatures 1 to 3 have the following problems.

Firstly, they each are formed as independent special and thus the resulting problems are present. Specifically, since they have individual structures as the special tools, both the part cost and the manufacturing cost are inevitably increased, and thus it is difficult to provide them as inexpensive products. Moreover, the structures tend to be complicated, and thus the durability thereof are unsatisfactory.

Secondly, the additional special tools are used by being fitted to a leg, and thus each time they are used, complicated fitting operations and, removing operations are needed. Hence, for example, handling and usability are inferior, and thus customer convenience is unsatisfactory. Furthermore, it is difficult to acquire comfort at the time of use. In other words, since, a strong uncomfortable feeling is given when they are put on, and they are heavy, it is difficult to obtain a natural feeling of use. Moreover, it is difficult to walk in a state where they are fitted, and thus safety is also unsatisfactory.

An object of the present invention is to provide supporters which solve the problems present in the background art and a method of manufacturing such supporters.

Solution to Problem

In order to solve the foregoing problems, a supporter 1 according to the present invention at least partially includes a tubular cover portion 2 which covers a part Hc of a human body and which elastically expands and contracts, and a load addition pattern portion P that is adhered to at least a part of a half or more circumference in a circumferential direction Ff on a front surface 2f of the tubular cover portion 2 and that can supply a load of a predetermined magnitude to the part Hc of the human body when the part Hc of the human body to which the tubular cover portion 2 is fitted is moved is continuously formed of an elastic rubber material R.

On the other hand, in order to solve the foregoing problems, according to the present invention, there is provided a method of manufacturing a supporter that at least partially includes a tubular cover portion 2 which covers a part Hc of a human body and which elastically expands and contracts, where an elastic rubber material R is adhered to at least a part of a half or more circumference in a circumferential direction Ff on a front surface 2f of the tubular cover portion 2, and a load addition pattern portion P is continuously provided which can apply a load of a predetermined magnitude to the part Hc of the human body when the part Hc of the human body to which the tubular cover portion 2 is fitted is moved.

In a preferred aspect of the present invention, as the elastic rubber material R, a silicone rubber material Rc can be used. Furthermore, a part or the whole of the area of the load addition pattern portion P is formed with a mesh-shaped portion Pam and preferably a honeycomb shape Pamh. On the other hand, the load addition pattern portion P includes an X-shaped portion Px, an upper side Pxup and Pxuq of the X-shaped portion is extended to both left and right sides and is arranged in a position Xc on an upper side of the heel of a foot along the circumferential direction Ff and a lower side Pxdp and Pxdq of the X-shaped portion Px is extended to both the left and right sides and is arranged in the position Xd of the arch of the foot along the circumferential direction Ff. In this case, the tubular cover portion 2 can include at least a sock Ss. The load addition pattern portion P can be configured so as to include a ring portion Pr which surrounds a protruding portion Hp of the human body and a load addition portion Pa which is continuous with the ring portion Pr and which can apply the load of the predetermined magnitude to the part Hc of the human body when the part Hc of the human body to which the tubular cover portion 2 is fitted is moved. In this case, the tubular cover portion 2 can be fitted to a knee Hk of a leg or an ankle Hn, and the load addition portion Pa for the tubular cover portion 2 here includes a plurality of load addition member portions Pau, Pap, Paq and Pad or Pax, Pay and Paz, and parts of the load addition member portions Pau, Pap, Paq and Pad or Pax, Pay and Paz can be individually and continuously formed with the ring portion Pr. On the other hand, in a method of manufacturing a supporter, the tubular cover portion 2 is fitted to an outer circumferential surface 11f of a cylindrical platen portion 11, and while the cylindrical platen portion 11 is being rotated, the load addition pattern portion P using the silicone rubber material R can be subjected to screen printing. In the outer circumferential surface 11f of the cylindrical platen portion 11, a concave portion (including a hole portion) 11a or a step portion 11b for displacing a part Sxa and Sxb which hinders flatness in the tubular cover portion 2 that is fitted is preferably provided.

Advantageous Effects of Invention

With the supporter 1 and the manufacturing method described above and according to the present invention, the following remarkable effects are provided.

(1) The load addition pattern portion P is integral with the tubular cover portion 2 which covers the part Hc of the human body and which elastically expands and contracts, and thus the configuration of an independent special tool is not needed, with the result that it is possible to remove disadvantages produced because the special tool is independent. Specifically, since both the part cost and the manufacturing cost can be reduced, it is possible to provide the supporter as an inexpensive product. Moreover, the structure is simplified, and thus the supporter can contribute to the enhancement of durability.

(2) The tubular cover portion 2 is fitted to the user, and thus the load addition pattern portion P is also simultaneously fitted to the fixed position of the user. Hence, each time the supporter is used, complicated fitting and removing operations are not needed, and thus handling and usability are excellent, with the result that customer convenience can be enhanced. Moreover, it is possible to acquire comfort when the supporter is used. Specifically, since an uncomfortable feeling when the supporter is fitted is reduced, and the supporter is light-weight, it is possible to obtain a natural feeling of use, and it is easy to walk in a state where the supporter is fitted, with the result that safety is enhanced.

(3) In a preferred aspect, as the elastic rubber material R, the silicone rubber material Rc is used, and thus the present invention can be practiced at low cost by utilization of a generic material, and it is possible to form the satisfactory load addition pattern portion P which can sufficiently achieve the actions and effects of the present invention described previously by the physical properties of the silicone rubber material Rc.

(4) In a preferred aspect, a part or the whole of the area of the load addition pattern portion P is formed with the mesh-shaped portion Pam, and thus even when as the elastic rubber material R, for example, the silicone rubber material Rc is used, it is possible to easily and widely adjust the magnitude of a load applied to the human body, and thus it is possible to easily perform a more fine adjustment on the feeling of use including the comfort of wearing, with the result that it is possible to apply a load whose support is not too strong and not too weak and which is most suitable for the human body. In particular, the mesh-shaped portion Pam is formed in the honeycomb shape Pamh, and thus it is possible to apply a stable load in so-called three-dimensional directions.

(5) In a preferred aspect, in the formation of the load addition pattern portion P, an X-shaped portion Px is included, the upper sides Pxup and Pxuq of the X-shaped portion Px are extended to both left and right sides and are arranged in a position Xc on the upper side of the heel of the foot along the circumferential direction Ff and the lower sides Pxdp and Pxdq of the X-shaped portion Px are extended to both left and right sides and are arranged in a position Xd of the arch of the foot along the circumferential direction Ff, with the result that in particular, the load addition pattern portion P can be formed as a supporter for protecting the Achilles' heel of the foot and thus the tubular cover portion 2 is most suitable when it is applied to at least the sock Ss.

(6) In a preferred aspect, in the formation of the load addition pattern portion P, an ring portion Pr that surrounds a protruding portion Hp of the human body and a load addition portion Pa that is continuous with the ring portion Pr and that can apply a load of a predetermined magnitude to the part the of the human body when the part Hc of the human body to which the tubular cover portion 2 is fitted is moved are provided, and thus the ring portion Pr can be engaged with the protruding portion Hp of the human body when the tubular cover portion 2 is fitted, with the result that even in a case where the part Hc of the human body is significantly moved, it is possible to prevent the tubular cover portion 2 from being displaced and it is possible to apply a highly effective and stable load by the load addition portion Pa with the protruding portion Hp serving as the starting point.

(7) In a preferred aspect, the tubular cover portion 2 is formed such that the tubular cover portion 2 can be fitted to the knee Hk of the leg or the ankle Hn, and thus in particular, muscles and joints related to the knee Hk of the leg or the ankle Hn on which a burden is placed at the time of walking or running can be supported, with the result that it is possible to protect the muscles and joints and enhance their functions.

(8) In a preferred aspect, the load addition portion Pa is formed with a plurality of load addition member portions Pau, Pap, Paq and Pad or Pax, Pay and Paz, the parts of the load addition member portions Pau, Pap, Paq and Pad or Pax, Pay and Paz are continuously formed with the ring portion Pr and thus it is possible to allocate, to the load addition member portions Pau, Pap, Paq and Pad or Pax, Pay and Paz, functions corresponding to the positions, for example, various types of functions such as the function of reducing tightening so as to acquire a comfortable feeling of wearing, the function of preventing the displacement of the ring portion Pr and the like and the original function of applying a load in a specific direction, with the result that it is possible to form the suitable supporter 1 corresponding to the part to which the tubular cover portion 2 is fitted.

(9) In a preferred aspect, in a method of manufacturing a supporter, the tubular cover portion 2 is fitted to an outer circumferential surface 11*f* of a cylindrical platen portion 11, while the cylindrical platen portion 11 is being rotated, the load addition pattern portion P using the silicone rubber material R is subjected to screen printing and thus even in the supporter 1 having the tubular cover portion 2, the tubular cover portion 2 can be rotated with the cylindrical platen portion 11 that is fitted, with the result that it is possible to easily and satisfactorily print the load addition pattern portion P in the circumferential direction Ff on the front surface 2*f* of the tubular cover portion 2.

(10) In a preferred aspect, in the outer circumferential surface 11*f* of the cylindrical platen portion 11, a concave portion (including a hole portion) 11*a* or a step portion 11*b* for displacing parts Sxa and Sxb which hinder the flatness of the tubular cover portion 2 that is fitted is provided, and thus it is possible to displace the parts Sxa and Sxb from the front surface 2*f* to be printed, with the result that even when the heel portion (Sxa), the mouth rubber portion (Sxb) or the like is present, it is possible to reliably and stably perform printing in the circumferential direction Ff of the front surface 2*f* without the load addition pattern portion P being hindered by the parts Sxa and Sxb.

REFERENCE SIGNS LIST

1: supporter, 2: tubular cover portion, 2*f*: front surface of tubular cover portion, 11: cylindrical platen portion, 11*f*: outer circumferential surface of cylindrical platen portion, 11*a*: concave portion (including hole portion), 11*b*: step portion, Ff: circumferential direction, Hc: part of human body, Hp: protruding portion of human body, Hk: knee, Hn: ankle, R: elastic rubber material, Rc: silicone rubber material, P: load addition pattern portion, Pr: ring portion, Pa: load addition portion, Pam: mesh-shaped portion, Pamh: honeycomb shape, Pau: load addition member portion, Pap: load addition member portion, Paq: load addition member portion, Pad: load addition member portion, Pax: load addition member portion, Pay: load addition member portion, Paz: load addition member portion, Px; X-shaped portion, Pxup; upper side of X-shaped portion, Pxuq: upper side of X-shaped portion, Pxdp: lower side of X-shaped portion, Pxdq: lower side of X-shaped portion, Ss: sock, Sxa: part hindering flatness of tubular cover portion, Sxb: part hindering flatness of tubular cover portion, Xc: position on upper side of heel of foot, Xd: position of arch of foot.

DESCRIPTION OF EMBODIMENTS

Preferred embodiments according to the present invention will then be described in detail with reference to drawings.

First Embodiment

A sock Ss (supporter 1) according to a first embodiment will first be described with reference to FIGS. 1 to 6.

Figure 6:
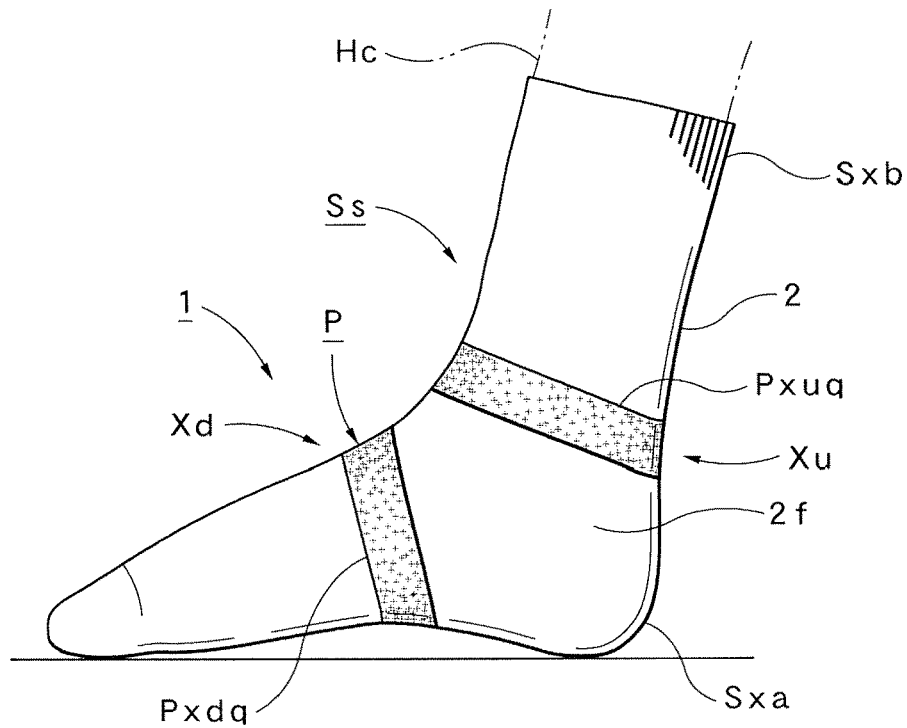
FIG. 6 is a side view showing a state where the sock is used.

The configuration of the sock Ss according to the first embodiment will first be described. As the sock Ss, a general sock which is commercially available as shown in FIG. 6 can be utilized as it is. Hence, a tubular cover portion 2 that covers a foot portion which is a part Hc of a human body and that elastically expands and contracts is included, and one end (tip end) of the tubular cover portion 2 is closed. The other end of the tubular cover portion 2 is opened, in the opening, a mouth rubber portion (Sxb) made by sewing is generally provided and in an intermediate part of the tubular cover portion 2, a heel portion (Sxa) is provided. The tubular cover portion 2 may naturally be manufactured as a tubular cover portion 2 specifically for the sock Ss according to the present embodiment.

Figure 1:
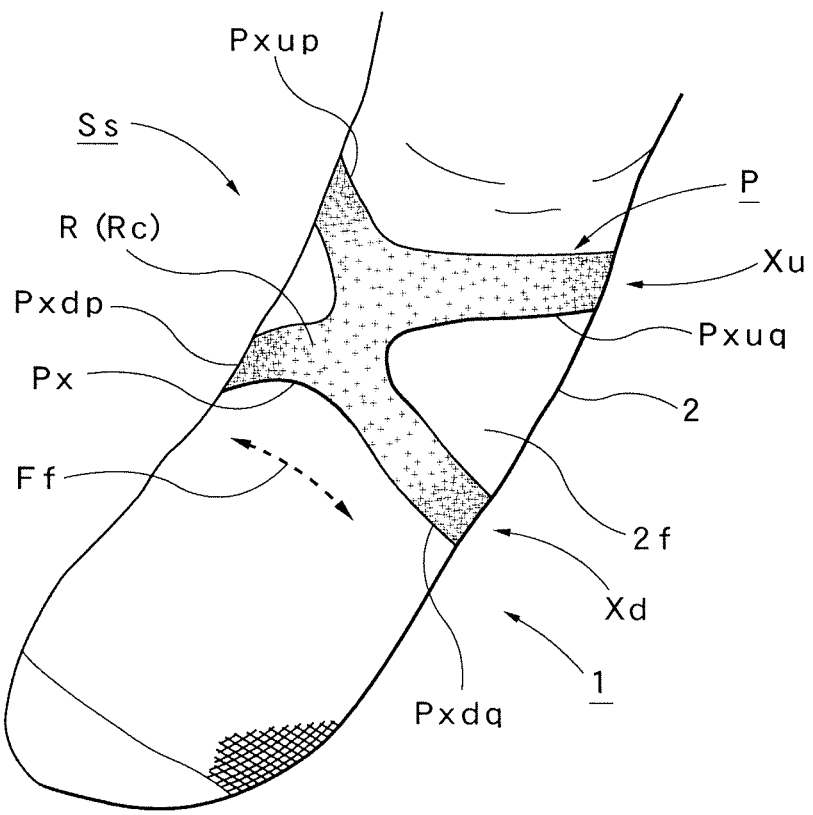
FIG. 1 is a perspective view showing a state of use where a sock according to a first embodiment of the present invention is worn.
Figure 2:
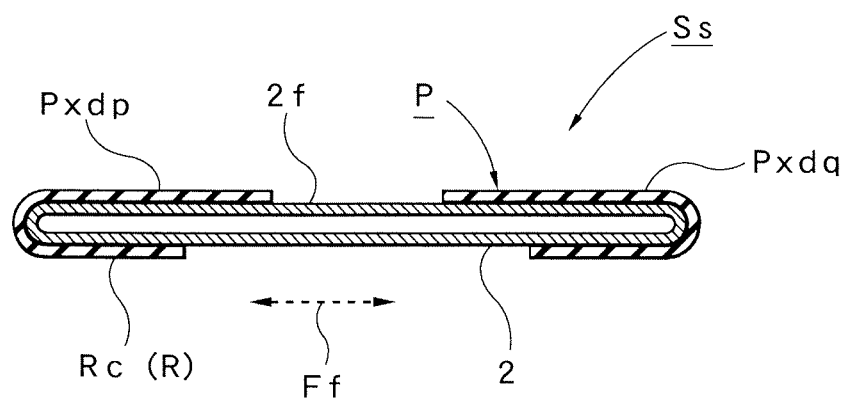
FIG. 2 is an end view of the sock taken long line A-A in FIG. 3.

On the front surface 2*f* of the tubular cover portion 2, a load addition pattern portion P that can apply a load (=tension) of a predetermined magnitude to the part Hc of the human body when the part Hc of the human body to which the tubular cover portion 2 is fitted is moved is continuously formed of a silicone rubber material Rc, and is provided on, at least a part of a half or more circumference in a circumferential direction Ff. As shown in FIG. 1, the illustrated load addition pattern portion P includes an X-shaped portion Px, the center of the X-shaped portion Px is arranged on the front surface of the tubular cover portion 2, upper sides Pxup and Pxuq of the X-shaped portion Px are extended to both left and right sides and are arranged in a position Xc on the upper side of the heel of the foot along the circumferential direction Ff and lower sides Pxdp and Pxdq of the X-shaped portion N are extended to both left and right sides and are arranged in a position Xd of the arch of the foot along the circumferential direction Ff. The load addition pattern portion P is formed in the shape described above, and thus as shown in FIG. 6, in particular, the load addition pattern portion P can be formed as a supporter for protecting the Achilles' heel of the foot when the sock Ss is fitted, with the result that the tubular cover portion 2 is most suitable when it is applied to at least the sock Ss.

Since the silicone rubber material Rc is used for the formation of the load addition pattern portion P, the present invention can be practiced at low cost by utilization of a generic material, and it is advantageously possible to form the satisfactory load addition pattern portion P which can sufficiently achieve the actions and effects of the present invention described previously by the physical properties of the silicone rubber material Rc. Furthermore, the load (tension) of the predetermined magnitude which can be applied (added) to the part Hc of the human body when the part Hc of the human body is moved can be set by at least one or two or more of the thickness of the load addition pattern portion P, the width of the load addition pattern portion P, the shape of the load addition pattern portion P, the number of load addition pattern portions P and the type of silicone rubber material Rc (elastic rubber material R).

Figure 3:
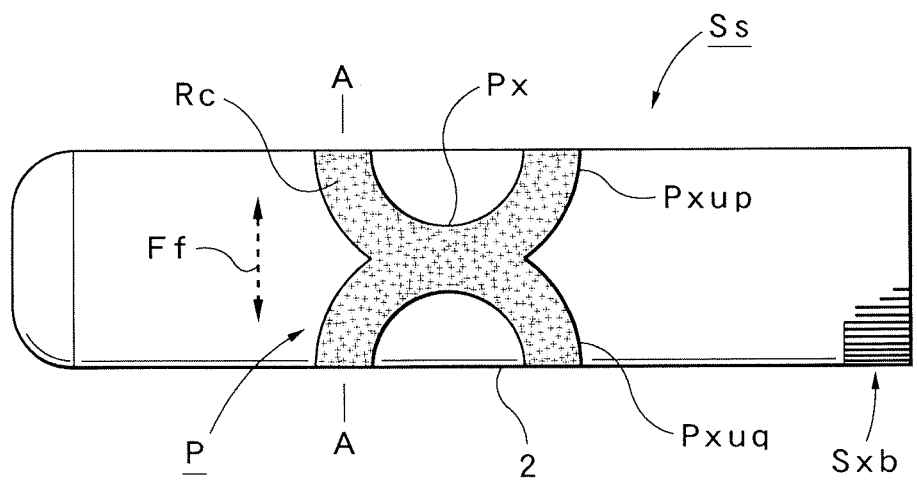
FIG. 3 is a plan view showing a state where the sock is not used.
Figure 4:
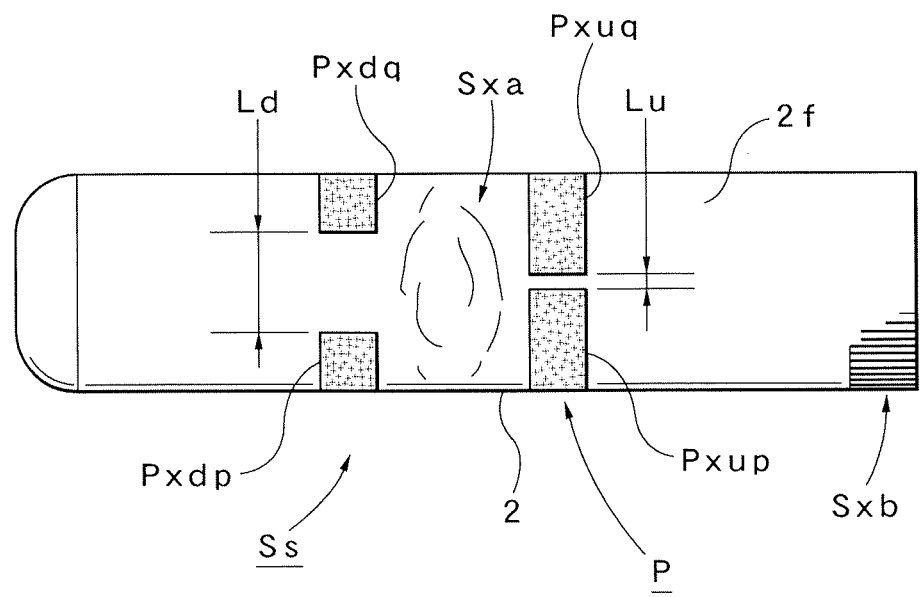
FIG. 4 is a bottom view showing a state where the sock is not used.

As shown in FIGS. 3 and 4, preferably, when the X-shaped portion Px is formed, between the end portions of the upper sides Pxup and Pxuq extended to both left and right sides, a predetermined distance Lu is set, and between the end portions of the lower sides Pxdp and Pxdq, a predetermined distance Ld is set. The distances Lu and Ld described above are set, and thus in particular, parts of the tubular cover portion 2 in which the load addition pattern portion P is not provided can be left, with the result that it is advantageously possible to easily perform a more fine adjustment on the feeling of use including the comfort of wearing by adjusting the distances Lu and Ld.

Figure 5:
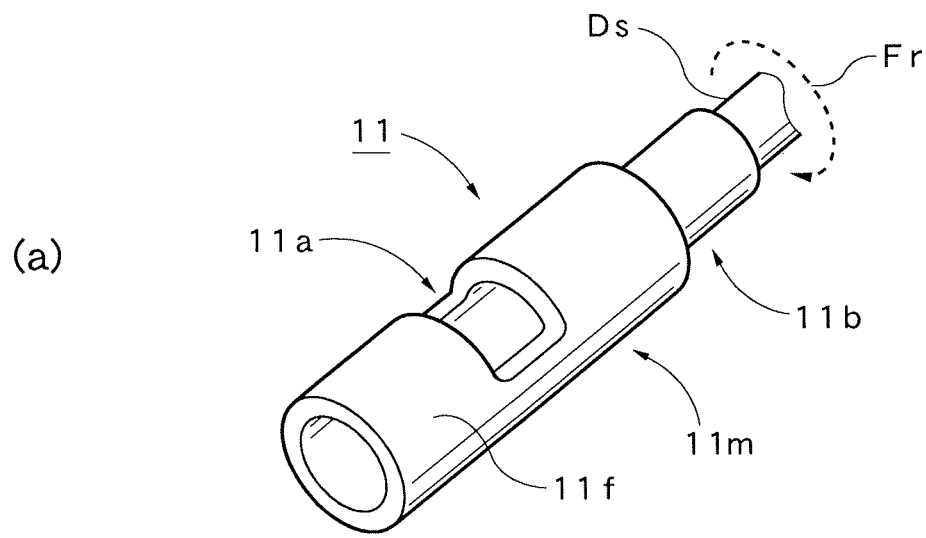
FIG. 5 is a process illustrative view for illustrating a method of manufacturing the sock.
Figure 5:
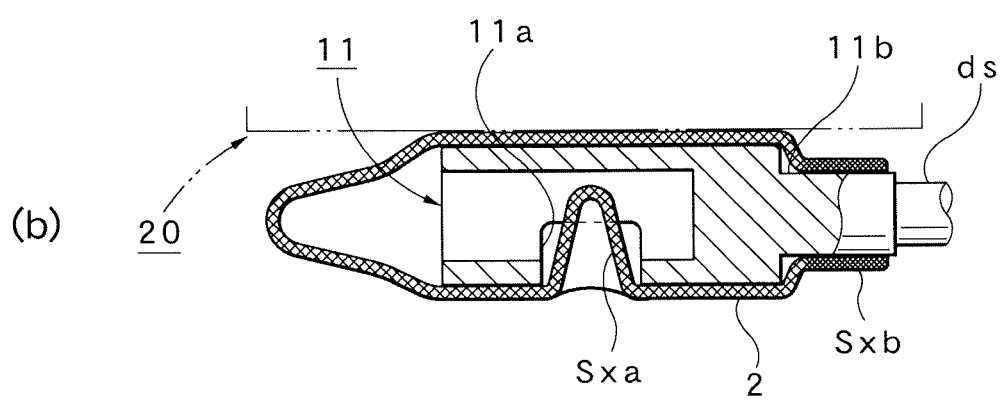
Figure 5:
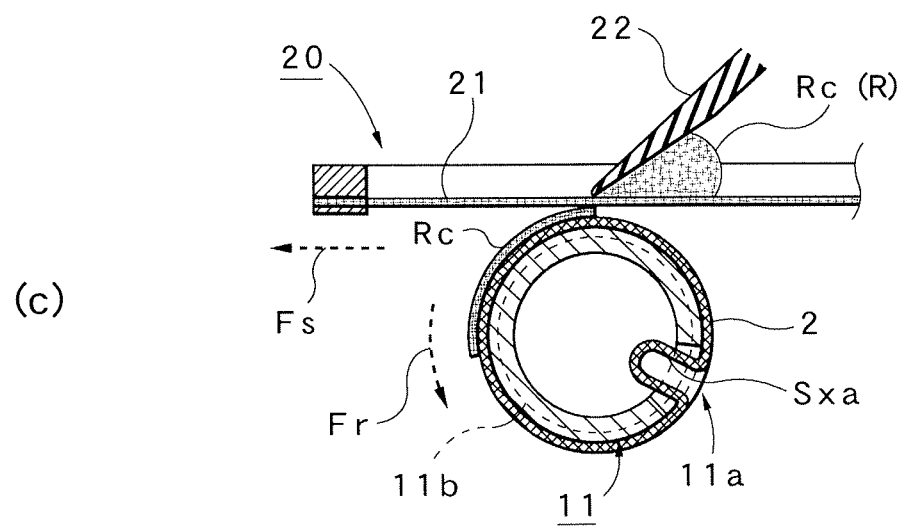

A method of manufacturing the sock Ss according to the first embodiment will then be sequentially described with reference to FIGS. 1 to 6, in particular, FIG. 5.

In the manufacturing of the sock Ss according to the first embodiment, a screen printing machine 20 shown in FIGS. 5(b) and 5(c) can be used. The screen printing machine 20 is particularly a screen printing machine for curved surface printing which performs printing on a cylindrical curved surface, and as shown in FIG. 5(c), the illustrated screen printing machine 20 includes a cylindrical platen portion 11, a screen 21 which is supported by a plate frame and a squeegee 22. Thus, the cylindrical platen portion 11 is rotated in the direction of an arrow Fr, and the screen 21 is moved forward (or moved backward) in the direction of an arrow Fs. The position of the squeegee 22 in a horizontal direction is fixed with respect to the cylindrical platen portion 11.

The structure (shape) of the cylindrical platen portion 11 is shown in FIG. 5(a). The cylindrical platen portion 11 includes a cylindrical body portion 11m, and in the outer circumferential surface 11f of the body portion 11m, a concave portion (including a hole portion) 11a or a step portion 11b for displacing parts Sxa and Sxb which hinder the flatness of the tubular cover portion 2 that is fitted. In the case of the sock Ss, the part Sxa which hinders the flatness is the heel portion, and the part Sxb is the mouth rubber portion. Hence, in the outer circumferential surface 11f, the hole portion 11a for displacing the part Sxa is formed, and the step portion 11b for displacing the part Sxb is formed. The hole portion 11a may be a concave portion or a step portion. The step portion 11b may be a hole portion or a concave portion. Since in the cylindrical platen portion 11, the concave portion (including the hole portion) 11a or the step portion 11b described above is provided, and thus it is possible to displace the parts Sxa and Sxb from the front surface 2f to be printed, even when as in the sock Ss, the heel portion (Sxa), the mouth rubber portion (Sxb) or the like is present, it is advantageously possible to reliably and stably perform printing in the circumferential direction 14 of the front surface 2f without the load addition pattern portion P being hindered by the parts Sxa and Sxb. Ds represents a rotation shaft.

In this case, with respect to the cylindrical platen portion 11, a plurality of cylindrical platen portions 11 which have a plurality of different outside diameters that match with the types of tubular cover portions 2 to be printed are previously prepared, and the cylindrical platen portion 11 is selected for each of the types of tubular cover portions 2 to be printed and is used. The types of tubular cover portions 2 include not only sizes of an M size, an L size and the like but also various types such as the fiber quality and the sewing method with which the tubular cover portion 2 is sewn.

On the other hand, as the screen 21, a screen on which a plate for printing the load addition pattern portion P described previously is formed is prepared, and on the upper surface of the screen 21, the silicone rubber material R to be used is set. Here, the screen 21 and the silicone rubber material Rc are previously set (adjusted), as described previously, by one or two or more of the thickness of the load addition pattern portion P, the width of the load addition patter portion P, the shape of the load addition pattern portion P, the number of load addition pattern portions P and the type of silicone rubber material Rc (including different viscosities and additives) such that the load addition pattern portion P obtained produces the load (tension) of the predetermined magnitude. When such a setting is performed, only the plate for printing is changed based on these dimensions, and thus it is possible to change the load. Hence, it is advantageously possible not only to easily provide the load addition pattern portion P which has the load of the predetermined magnitude and but also to easily perform optimization.

A specific method of printing (coating method) the load addition pattern portion P will be described below. First, as shown in FIG. 5(b), the tubular cover portion 2 is set on the outer circumferential surface 11f of the cylindrical platen portion 11 in the screen printing machine 20. In this case, the cylindrical platen portion 11 is inserted into the tubular cover portion 2, and thus the heel portion, that is, the part Sxa which hinders the flatness in the tubular cover portion 2 is held in the hole portion 11a of the cylindrical platen portion 11, and the mouth rubber portion, that is, the part Sxb which hinders the flatness is located in the step portion 11b of the cylindrical platen portion 11.

Then, the screen 21 is set in a fixed position with respect to the cylindrical platen portion 11 on which the tubular cover portion 2 is set. Hence, the rotation start position of the cylindrical platen portion 11 in the rotation direction and the movement start position of the screen 2 are located in a home position, and thus the start positions coincide with each other. Thereafter, as shown in FIG. 5(c), the cylindrical platen portion 11 is rotated at a predetermined speed in the direction of the arrow Fr, and the screen 21 is moved forward (moved horizontally) in the direction of the arrow Fs. The rotation movement and the forward movement here are synchronized with each other. The position of the squeegee 22 is fixed. In this way, the front surface 2f of the tubular cover portion 2 is coated with the load addition pattern portion P by screen printing. In other words, on the front surface 2f, the load addition pattern portion P is continuously formed on the front surface 2f.

After the completion of the printing, the screen 21 is returned to a release position. Then, in a state where the tubular cover portion 2 is set on the cylindrical platen portion 11, dry processing is performed so as to cure the silicone rubber material Rc. In this case, natural dry processing may be performed or forced dry processing by heating may be performed. When a set time elapses, the dry processing is completed, and then the tubular cover portion 2 is released from the cylindrical platen portion 11. In this way, it is possible to obtain the sock Ss which is shown in FIGS. 3 and 4 and in which the load addition pattern portion P is integrally provided.

A method of using the sock Ss according to the first embodiment and the function thereof will then be described with reference to FIGS. 1 to 6.

Since the sock Ss according to the first embodiment is obtained by integrally providing the load addition pattern portion P in a general sock, when the sock Ss is used, as shown in FIG. 6, the sock Ss can be put on by the same operation as when a user puts on a sock on the leg of the user, and thus at the same time, the load addition pattern portion P can be fitted to the intended fixed position in the leg.

As described previously, the supporter serving as the special tool corresponding to the load addition pattern portion P is known, and thus the load addition pattern portion P according to the first embodiment can achieve the same function as the supporter serving as the special tool. Specifically, in a state where the sock Ss is worn, as shown in FIGS. 1 to 6, the center of the X-shaped portion Px in the load addition pattern portion P is located on the front surface of the tubular cover portion 2. The upper sides Pxup and Pxuq of the X-shaped portion Px are extended to both left and right sides and are arranged in the position Xc on the upper side of the heel of the foot along the circumferential direction Fr and the lower sides Rxdp and Rxdq of the X-shaped portion Px are also extended to both left and right sides and are arranged in the position Xd of the arch of the foot along the circumferential direction Ff.

Hence, when the user wearing the sock Ss moves the part Hc of the human body, for example, when the user walks, the load (tension) of the predetermined magnitude can be applied to the part Hc of the human body, and in addition to the original function of the sock, as with the supporter serving as the special tool, the sock Ss can be made to function as the supporter for protecting the Achilles' heel of the foot and the like.

As described above, in the sock Ss according to the first embodiment, the load addition pattern portion P is integral with the sock Ss (the body of the sock) having the tubular cover portion 2 which covers the part Hc of the human body and which elastically expands and contracts, and thus the configuration of an independent special tool is not needed, with the result that it is possible to remove disadvantages produced because the special tool is independent. Specifically, since both the part cost and the manufacturing cost can be reduced, it is possible to provide the sock Ss as an inexpensive product. Moreover, the structure is simplified, and thus the sock Ss can contribute to the enhancement of durability. Furthermore, the sock Ss having the tubular cover portion 2 is fitted to the user, and thus the load addition pattern portion P is also fitted to the fixed position of the user. Hence, each time the sock Ss is used, complicated fitting and removing operations, are not needed, and thus customer convenience such as excellent handling and usability can be enhanced. Moreover, it is possible to acquire comfort when the sock Ss is used. Specifically, since an uncomfortable feeling when the sock Ss is fitted is reduced, and the sock Ss is light-weight, it is possible to obtain a natural feeling of use, and it is easy to walk in a state where the sock Ss is fitted, with the result that safety is enhanced.

Figure 7:
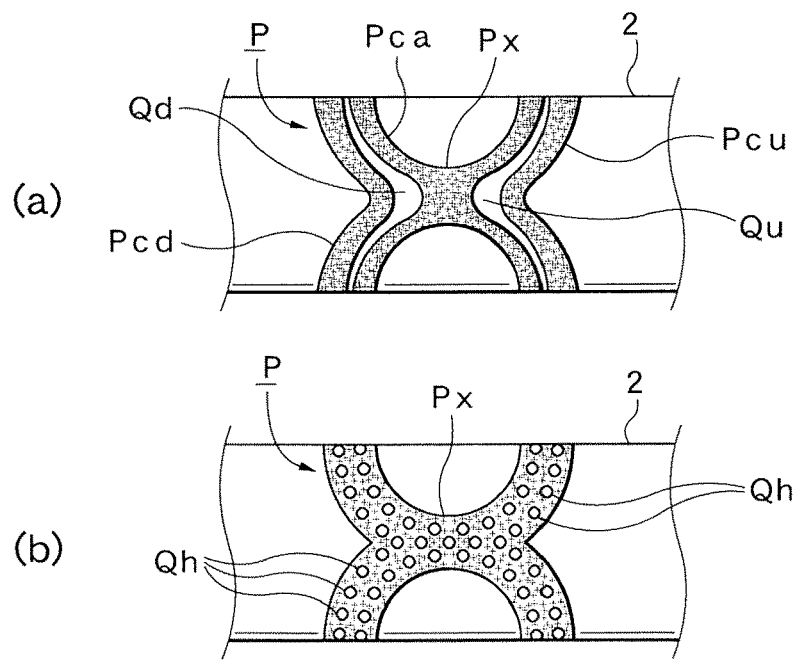
FIG. 7 is a plan view showing variations of a load addition pattern portion in the sock.

FIGS. 7(a) and 7(b) show variations of the load addition pattern portion P. FIG. 7(a) shows the variation where in the basic load addition pattern portion P shown in FIG. 1, slit portions Qu and Qd are provided in a left/right direction, and where thus the load addition pattern portion P is divided into three load addition pattern portion members Pa, Pu and Pd. FIG. 7(b) shows the variation where in the basic load addition pattern portion P shown in FIG. 1, a large number of small holes Qh are provided.

As described above, the load addition pattern portion P can be practiced with various pattern portions such as those of FIGS. 1, 7(a) and 7(b) shown as examples. In this case, it is possible to easily make a change such as by changing the plate in the printing. In FIGS. 7(a) and 7(b), the same portions (including the same functional portions) as in FIGS. 1 to 6 are identified with the same symbols, and thus the configurations thereof are clarified, and the detailed description thereof will be omitted.

Second Embodiment

A supporter for a knee Sk (supporter 1) according to a second embodiment will then be described with reference to FIGS. 8 to 12.

Figure 8:
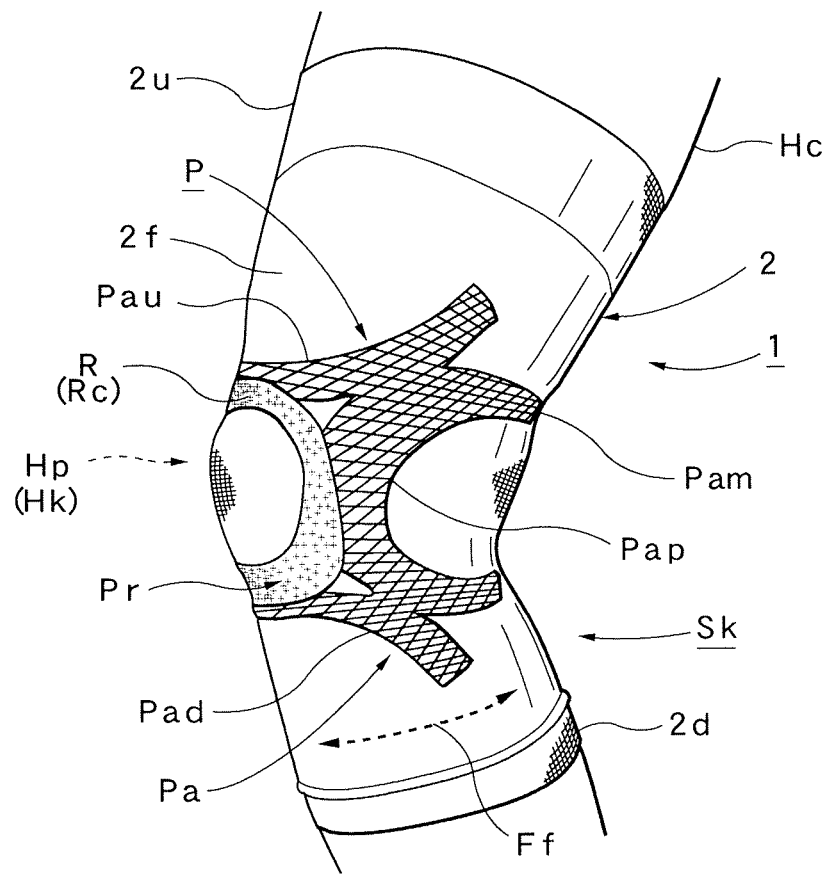
FIG. 8 is a perspective view showing a state of use, where a supporter for a knee according to a second embodiment of the present invention is fitted to the knee of a leg.

The configuration of the supporter for the knee Sk according to the second embodiment will first be described. As with the sock Ss described in the first embodiment, as the supporter for the knee Sk, a general supporter for a knee which is commercially available as shown in FIG. 8 can be utilized as it is. Hence, a tubular cover portion 2 that covers a knee Hk which is a part Hc of a human body and that elastically expands and contracts is included, both ends of the tubular cover portion 2 are opened and in each of openings, mouth rubber portions (2u and 2d) made by sewing are generally provided. The tubular cover portion 2 may naturally be manufactured as a tubular cover portion 2 specifically for the supporter for the knee Sk according to the present embodiment. On the front surface 2f of the tubular cover portion 2, a load addition pattern portion P shown in FIG. 9 that can apply a load of a predetermined magnitude to the part Hc of the human body when the part Ile of the human body to which the tubular cover portion 2 is fitted is moved is continuously formed of a silicone rubber material Rc (elastic rubber material R), and is provided on at least apart of a half or more circumference in a circumferential direction Ff. As described above, the tubular cover portion 2 is fitted such that the tubular cover portion 2 can be fitted to the knee Hk of the leg, and thus in particular, muscles and joints related to the knee Hk of the leg on which a burden is placed at the time of walking or running can be supported, with the result that it is possible to protect the muscles and joints and enhance their functions.

As shown, in FIG. 8, the specific shape of the load addition pattern portion P is formed with a ring portion Pr that surrounds the knee Hk which is a protruding portion Hp of a human body and a load addition portion Pa that is continuous with the ring portion Pr and that can apply a load of a predetermined magnitude to the knee Hk when the knee Hk to which the tubular cover portion 2 is fitted is moved. In the configuration described above, since the ring portion Pr can be engaged with the knee Hk when the tubular cover portion 2 is fitted, even in a case where the knee Hk is significantly moved, it is possible to prevent the tubular cover portion 2 from being displaced, and it is advantageously possible to apply a highly effective and stable load by the load addition portion Pa with the protruding portion Hp serving as the starting point, that is, with the knee Hk serving as the starting point.

In this case, the ring portion Pr is formed in the shape of an egg which has a predetermined ring width. In this way, when the ring portion Pr is fitted to the knee Hk, the ring portion Pr is arranged so as to surround the knee Hk which is the protruding portion Hp of the human body. In particular, since the silicone rubber material Rc is adhered to the entire ring portion Pr, when the ring portion Pr is enlarged by being stretched, the ring portion Pr can make a relatively large load for the engagement act on the protruding portion Hp.

Figure 9:
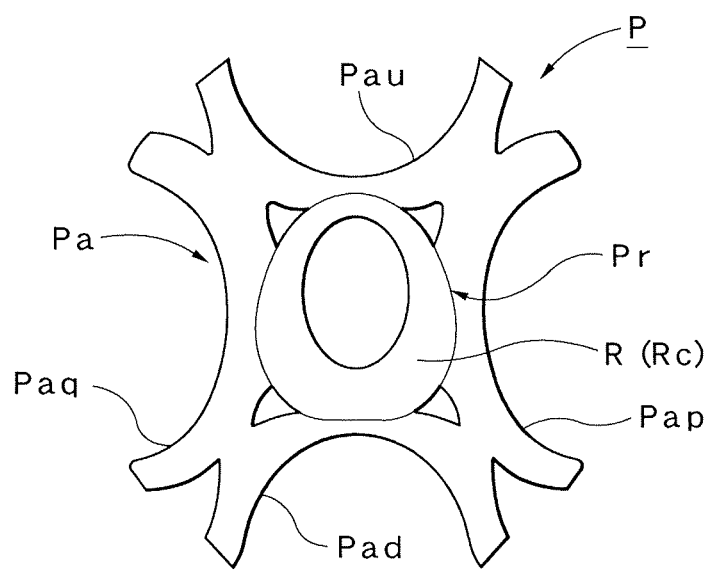
FIG. 9 is an exploded view of a load addition pattern portion in the supporter for a knee.
Figure 10:
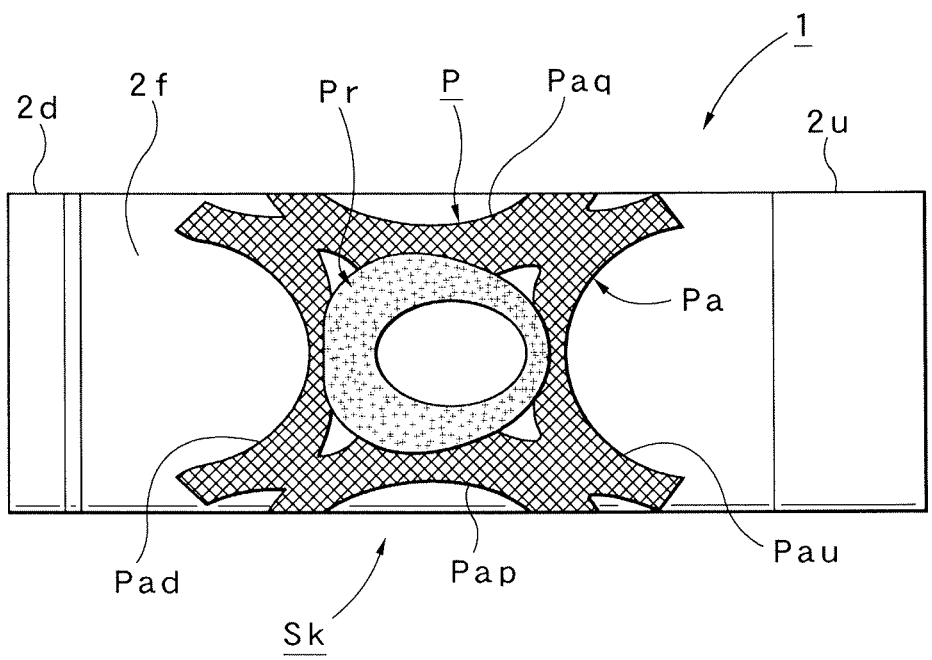
FIG. 10 is a front view showing a state where the supporter for a knee is not used.
Figure 11:
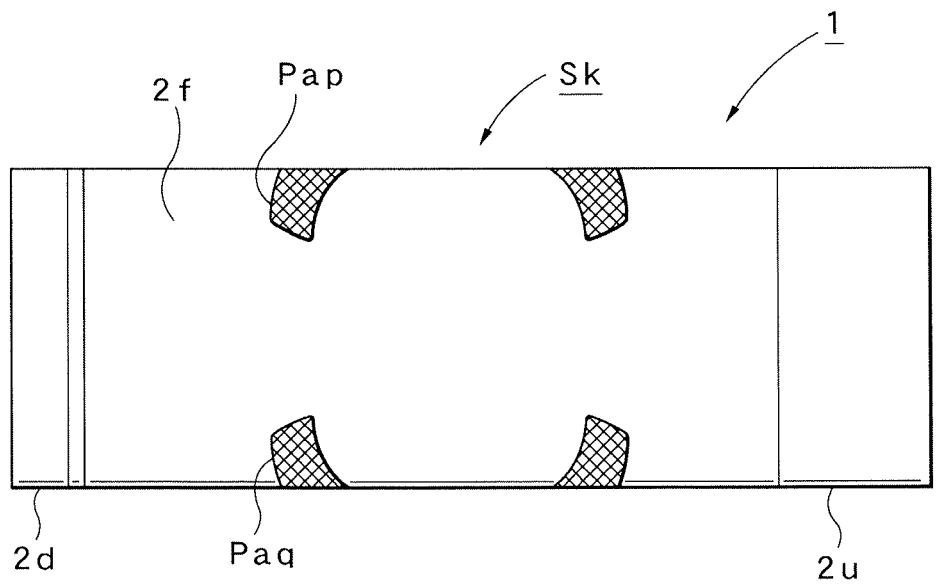
FIG. 11 is a back view showing a state, where the supporter for a knee is not used.

On the other hand, as shown in FIG. 9, the load addition portion Pa includes four load addition member portions Pau, Pap, Paq and Pad which are formed in the shape of a half arch (bow shape) having a predetermined width or which are formed in a shape similar thereto. The load addition member portions Pau, Pap, Paq and Pad are respectively arranged on the upper side, the left side, the right side and the lower side of the ring portion Pr, parts of the load addition member portions Pau, Pap, Paq and Pad, that is, the center parts thereof are continuously formed with the ring portion Pr and as shown in FIG. 12, parts of the load, addition member portions Pan, Pap, Paq and Pad adjacent to each other are continuously formed.

The entire area of the load addition member portions Pau, Pap, Paq and Pad forming the load addition portion Pa is formed with a mesh-shaped portion Pam. In this way, the magnitude of a load in a direction of return when the load addition portion Pa is stretched is lower than the ring portion Pr described previously. Hence, even when as the elastic rubber material the illustrated silicone rubber material Rc is used, it is possible to easily and widely adjust the magnitude of a load applied to the human body, and thus it is possible to easily perform a more fine adjustment an the feeling of use including the comfort of wearing, with the result that it is possible to apply a load whose support is not too strong and not too weak and which is most suitable for the human body.

Figure 12:
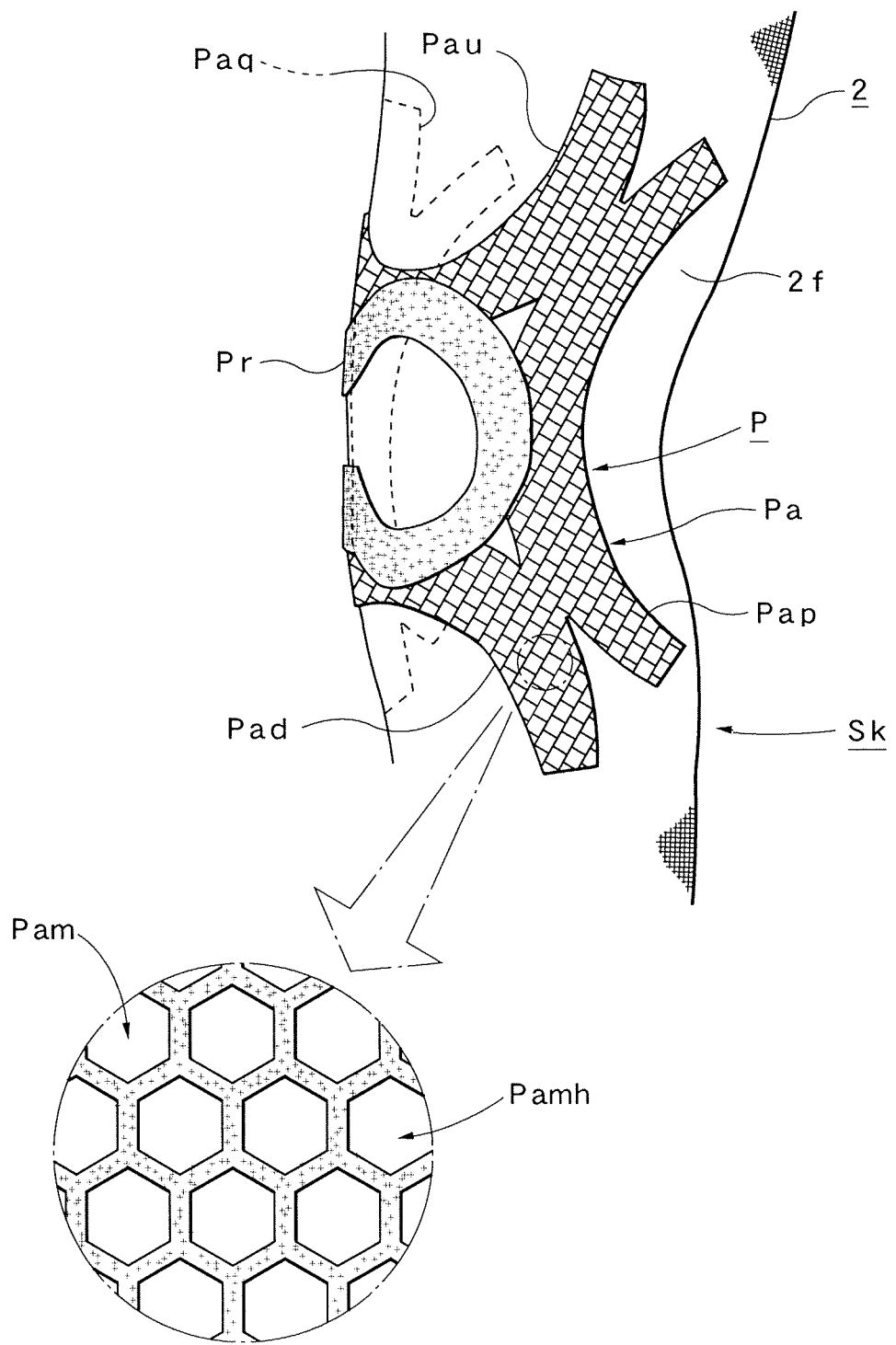
FIG. 12 is an illustrative view of a mesh-shaped portion of the supporter for a knee.

In this case, in particular, it is most suitable to form the mesh-shaped portion Pam in a honeycomb shape Pamh as shown in FIG. 12. As described above, the mesh-shaped portion Pam is formed in the honeycomb shape Pamh, and thus it is advantageously possible to apply a stable load in so-called three-dimensional directions.

As described above, the load addition portion Pa is formed with the four load addition member portions Pau, Pap, Paq and Pad, the parts of the load addition member portions Pau, Pap, Paq and Pad are continuously formal with the ring portion Pr and thus it is possible to allocate, to the load addition member portions Pau, Pap, Paq and Pad, functions corresponding to the positions, for example, various types of functions such as the function of reducing tightening so as to acquire a comfortable feeling of wearing, the function of preventing the displacement of the ring portion Pr and the like and the original function of applying a load in a specific direction, with the result that it is advantageously possible to form the suitable supporter for the knee Sk corresponding to the part to which it is fitted.

A method of manufacturing the supporter for the knee Sk according to the second embodiment, a method of using it and the function thereof will be described with reference to FIGS. 8 to 14.

Figure 13:
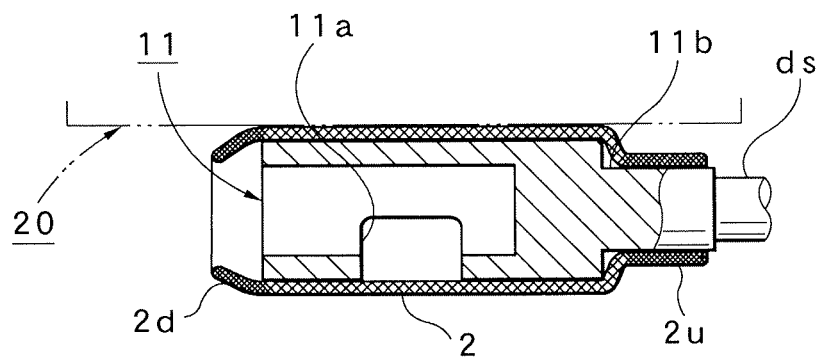
FIG. 13 is a process illustrative view for illustrating a method of manufacturing the supporter for a knee.

The supporter for the knee Sk can also be manufactured with the screen printing machine 20 shown in FIGS. 5(a) to 5(c). Since the supporter for the knee Sk and the sock Ss partially differ in the basic form, a state where the supporter for the knee Sk is fitted to the cylindrical platen portion 11 is shown in FIG. 13. Although as shown in FIG. 13, the state differs from the state of FIG. 5(b) described previously, except such differences, the basic method of manufacturing the supporter for the knee Sk is the same as the procedure for manufacturing the sock Ss described based on FIGS. 5(a) to 5(c).

Figure 14:
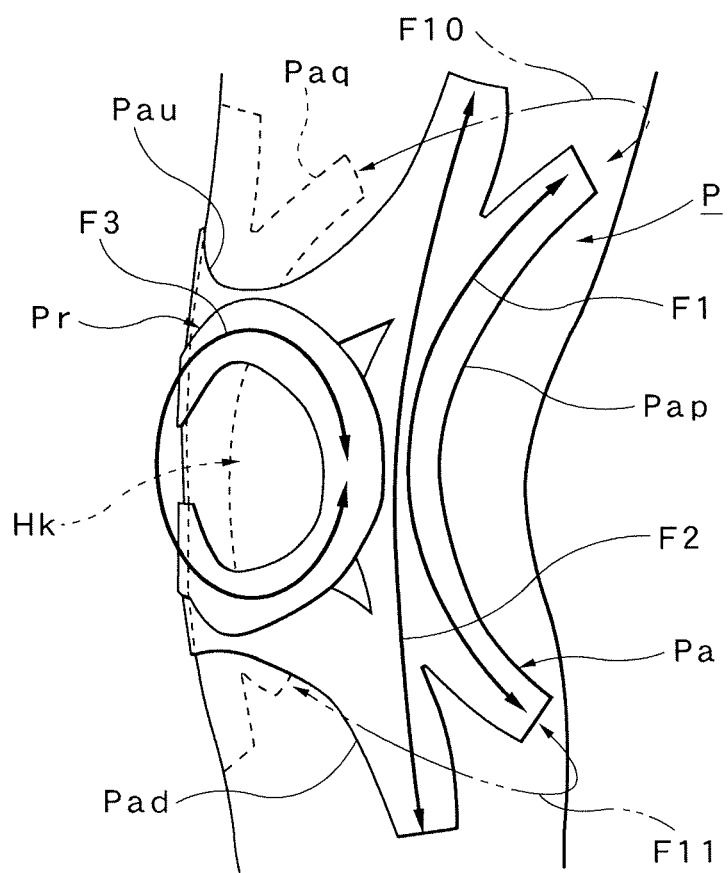
FIG. 14 is an illustrative view of the action of the supporter for a knee.

On the other hand, when the supporter for the knee Sk is used, as shown in FIG. 8, the supporter for the knee Sk can be fitted by the same operation as when a general supporter for a knee formed with only the tubular cover portion 2 is fitted to the knee Hk of the user. In this way, at the same time, the load addition pattern portion P can be fitted to the intended fixed position in the knee Hk. When the supporter for the knee Sk is fitted, as shown in FIG. 14, the ring portion Pr is engaged with the knee Hk which is the protruding portion Hp of the human body. Here, since the silicone rubber material Rc is adhered to the entire ring portion Pr, when the ring portion Pr is enlarged by being stretched, the ring portion Pr can make a relatively large load for the engagement act on the protruding portion Hp, with the result that for example, even when the knee Hk is significantly moved, it is possible to prevent the tubular cover portion 2 from being displaced. The direction of arrows F3 indicates the main direction in which the load exerted by the ring portion Pr acts.

Furthermore, as shown in FIG. 14, a load in the direction of arrows F2 exerted by the mesh-shaped portion Pam in the load addition portion Pa is added along the line of the leg to the human body. In other words, when the knee Hk is bent and stretched, it is possible to apply a highly effective and stable load by the load addition portion Pa with the protruding portion Hp serving as the starting point. The direction of arrows F1 is the direction of a load along the load addition member portions Pap and Paq which are arranged on the side surfaces on the left and right sides of the leg and which are formed in the shape of a bow, and extension lines on the tip ends of the load addition member portions Pap and Paq are continuous with each other along the direction of arrows F10 and the direct of arrows F11, with the result that this section is a so-called neutral zone where only the tubular cover portion 2 is present without the presence of the load addition pattern portion P. In this way, by the load exerted by the load addition member portions Pap and Paq and the reduction of tightening caused by the neutral zone, the prevention of displacements vertically and laterally and the appropriate degree of intimate contact (fitting) are acquired.

As described above, even in the supporter for the knee Sk according to the second embodiment, the load addition pattern portion P is integral with the tubular cover portion 2 which covers the pan Hc of the human body and which elastically expands and contracts, and thus the configuration of an independent special tool is not needed, with the result that it is possible to remove disadvantages produced because the special tool is independent. Specifically, since both the part cost and the manufacturing cost can be reduced, it is possible to provide the supporter for the knee Sk as an inexpensive product. Moreover, the structure is simplified, and thus the supporter for the knee Sk can contribute to the enhancement of durability. Furthermore, the tubular cover portion 2 is fitted to the user, and thus the load addition pattern portion P is also simultaneously fitted to the fixed position of the user. Hence, each time the supporter for the knee Sk is used, complicated fitting and removing operations are not needed, and thus handling and usability at excellent, with the result that customer convenience can be enhanced. Moreover, it is possible to acquire comfort when the supporter for the knee Sk is used. Specifically, since an uncomfortable feeling when the supporter for the knee Sk is fitted is reduced, and the supporter for the knee Sk is light-weight, it is possible to obtain a natural feeling of use, and it is easy to walk in a state where the supporter for the knee Sk is fitted, with the result that safety is enhanced. In other words, it is possible to obtain these basic effects.

Third Embodiment

A supporter fir an ankle Sn (supporter 1) according to a third embodiment will then be described with reference to FIGS. 15 to 18.

Figure 15:
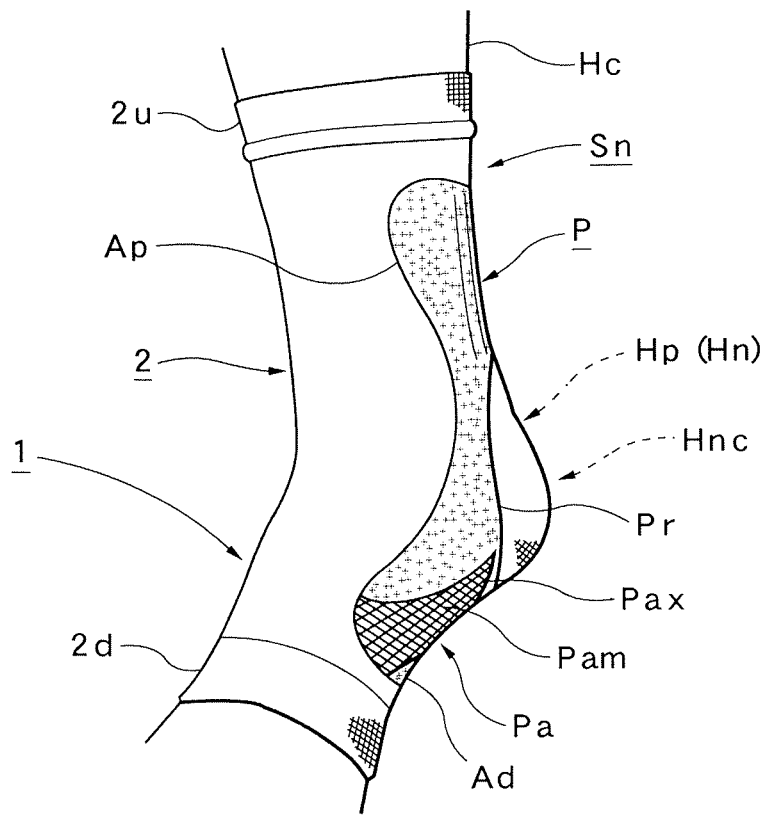
FIG. 15 is a perspective view showing a state of use where a supporter for an ankle according to a third embodiment of the present invention is fitted to an ankle.

The configuration of the supporter for the ankle Sn according to the third embodiment will first be described. As with the supporter for the knee Sk described in the second embodiment, as the supporter for the ankle Sn, a general supporter for an ankle which is commercially available as shown in FIG. 15 can be utilized as it is. Hence, a tubular cover portion 2 that covers an ankle Hn which is a part Hc of a human body and that elastically expands and contracts is included, both ends of the tubular cover portion 2 are opened and in each of openings, mouth rubber portions (2u and 2d) made by sewing are generally provided. The tubular cover portion 2 may naturally be manufactured as a tubular cover portion 2 specifically for the supporter for the ankle Sn according to the present embodiment. On the front surface 2f of the tubular cover portion 2, a load addition pattern portion P that can apply a load of a predetermined magnitude to the part Hc of the human body when the part Hc of the human body to which the tubular cover portion 2 is fitted is moved is continuously formed of a silicone rubber material Rc (elastic rubber material R), and is provided on at least a part of a half or more circumference in a circumferential direction Ff. As described above, the tubular cover portion 2 is formed such that the tubular cover portion 2 can be fitted to the ankle Hn, and thus in particular, muscles and joints related to the ankle Hn on which a burden is placed at the time of walking or running can be supported, with the result that it is possible to protect the muscles and joints and enhance their functions.

As shown in FIG. 15, the specific shape of the load addition pattern portion P is toted with a ring portion Pr that surrounds the ankle Hn (heel Hnc) which is a protruding portion Hp of a human body and a load addition portion Pa that is continuous with the ring portion Pr and that can apply a load of a predetermined magnitude to the ankle Hn when the ankle Hn to which the tubular cover portion 2 is fitted is moved. In the configuration described above, since the ring portion Pr can be engaged with the ankle Hn when the tubular cover portion 2 is fitted, even in a case where the ankle Hn is significantly moved, it is possible to prevent the tubular cover portion 2 from being displaced, and it is advantageously possible to apply a highly effective and stable load by the load addition portion Pa with the protruding portion Hp serving as the starting point, that is, with the heel Hnc serving as the starting point.

Figure 16:
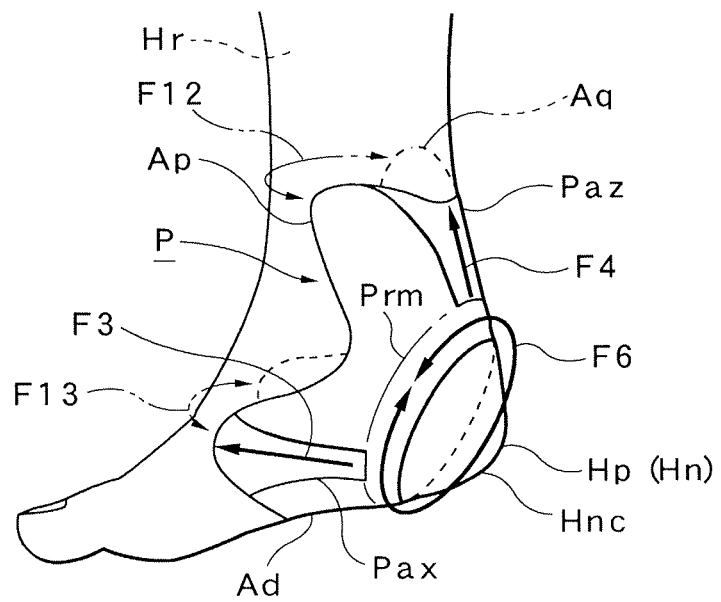
FIG. 16 is an illustrative view of the action of the supporter for an ankle.

In this case, as shown in FIG. 16, the ring portion Pr has, as a basic area, a ring area Prm which has a predetermined ring width, furthermore, on the left and right sides, extension areas Ap and Aq which individually have predetermined areas and shapes are integrally and continuously formed and on the lower side (bottom surface), an extension area Ad which has an area and a shape that are predetermined is integrally and continuously formed. In this way, when the ring portion Pr is fitted to the ankle Hn, the ring portion Pr is arranged so as to surround the heel fine of the ankle Hn which is the protruding portion Hp of the human body. In particular, since the silicone rubber material Rc is adhered to the entire ring portion Pr, when the ring portion Pr is enlarged by being stretched, the ring portion Pr can make a relatively large load for the engagement act on the protruding portion Hp.

Figure 17:
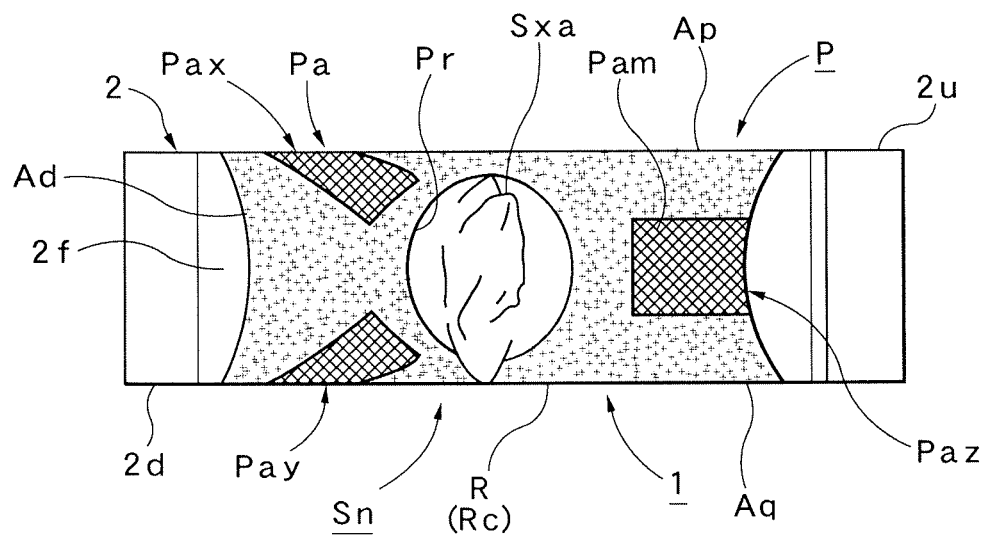
FIG. 17 is a back view showing, a state where the supporter for an ankle is not used.
Figure 18:
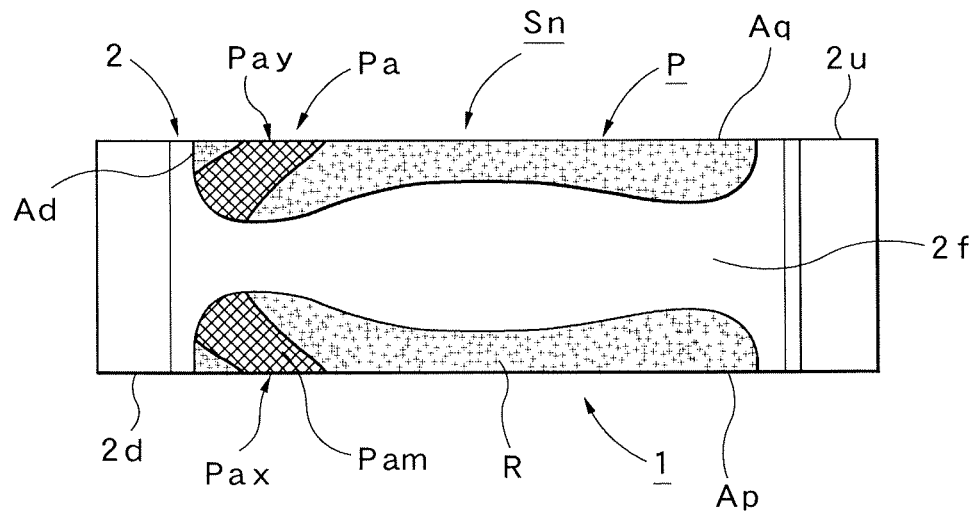
FIG. 18 is a front view showing a state where the supporter for an ankle is not used.

On the other hand, as shown in FIG. 17, the load addition portion Pa includes three load addition member portion Pax, Pay and Paz. The load addition member portion Pax is continuously formed between the extension areas Ap and Ad, the load addition member portion Pay is continuously formed between the extension areas Aq and Ad and furthermore, the load addition member portion Paz is continuously formed between the extension areas Ap and Aq. In this way, the load addition member portions Pax, Pay and Paz are respectively arranged on the left side, the right side and the upper side (back side) of the ring portion Pr. In this configuration, the extension areas Ap and Aq are brought into intimate contact with the left and right sides of the ankle an so as to hold the side surfaces of the leg, and the extension area Ad is brought into intimate contact with the bottom surface (the portion of the arch) of the foot so as to hold the bottom surface.

The entire area of the load addition member portions Pax, Pay and Paz is formed with a mesh-shaped portion Pam. In this way, the magnitude of a load in a direction of return when the load addition portion Pa is stretched is lower than the ring portion Pr described previously. Hence, even when as the elastic rubber material R, the illustrated silicone rubber material Rc is used, it is possible to easily and widely adjust the magnitude of a load applied to the human body, and thus it is possible to easily perform a more in adjustment on the feeling of use including the comfort of wearing, with the result that it is possible to apply a load whose support is not too strong and not too weak and which is most suitable for the human body. In this case, it is most suitable to form the mesh-shaped portion Pam in the honeycomb shape Pamh as shown in FIG. 12. The mesh-shaped portion Pam is formed in the honeycomb shape Pamh, and thus it is possible to apply a stable load in so-called three-dimensional directions.

As described above, the load addition portion Pa is formed with the three load addition member portions Pax, Pay and Paz, the parts of the load addition member portions Pax, Pay and Paz are continuously formed with the ring portion Pr and thus it is possible to allocate, to the load addition member portions Pau, Pap, Paq and Pad, functions corresponding to the positions, for example, various types of functions such as the function of reducing tightening so as to acquire a comfortable feeling of wearing, the function of preventing the displacement of the ring portion Pr and the like and the original function of applying a load in a specific direction, with the result that it is advantageously possible to form the suitable supporter for the ankle Sn corresponding to the part to which it is fitted.

A method of manufacturing the supporter for the ankle Sn according to the third embodiment, a method of using it and the function thereof will be described with reference to FIGS. 15 to 18.

The supporter for the ankle Sn can also be manufactured with the screen printing machine 20 shown in FIGS. 5(a) to 5(c), and the basic method of manufacturing the supporter for the ankle Sn is the same as the procedure for manufacturing the sock Ss described based on FIGS. 5(a) to 5(c). On the other hand, when the supporter for the ankle Sn is used, as shown in FIG. 15, the supporter for the ankle Sn can be fitted by the same operation as when a general supporter for an ankle formed with only the tubular cover portion 2 is fitted to the ankle Hn of the user. In this way, at the same time, the load addition pattern portion P can be fitted to the intended fixed position in the ankle Hn. When the supporter for the ankle Sn is fitted, as shown in FIG. 15, the ring portion Pr is engaged with the heel line of the ankle Hn which is the protruding portion Hp of the human body. Here, since the silicone rubber material Rc is adhered to the entire ring portion Pr, when the ring portion. Pr is enlarged by being stretched, the ring portion Pr can make a relatively large load for the engagement act on the protruding portion Hp, with the result that for example, even when the ankle Hn significantly moved, it is possible to prevent the tubular cover portion 2 from being displaced. The direction of arrows F6 indicates the main direction in which the load exerted by the ring portion Pr acts.

The directions of arrows F3 and F4 in the load addition portion Pa along the line of the leg shown in FIG. 16 indicate the direction in which the load exerted by the mesh-shaped portion Pam acts when the ankle Hn is moved. As described above, it is possible to apply a highly effective and stable load by the load addition portion Pa with the protruding portion Hp serving as the starting point.

The direction of arrows F12 indicates extension lines on the tip ends of the extension areas Ap and Aq located on the left and right sides, and the extension lines are continuous with each other through the tubular cover portion 2, and the direction of arrows F13 indicates extension lines on the tip ends of the load addition member portions Paa and Pay located on the left and right sides, and the extension lines are continuous with each other through the tubular cover portion 2. This section is a so-called neutral zone where only the tubular cover portion 2 is present without the presence of the load addition pattern portion P. In this way, by the load exerted by the load addition member portions Pax, Pay and Paz and the reduction of tightening caused by the neutral zone, the prevention of displacements vertically and laterally and the appropriate degree of intimate contact (fitting) are acquired.

As described above, even in the supporter for the ankle Sn according to the third embodiment, the load addition pattern portion P is integral with the tubular cover portion 2 which covers the part Hc of the human body and which elastically expands and contracts, and thus the configuration of an independent special tool is not needed, with the result that it is possible to remove disadvantages produced because the special tool is independent. Specifically, since both the part cost and the manufacturing cost can be reduced, it is possible to provide the supporter for the ankle Sn as an inexpensive product. Moreover, the structure is simplified, and thus the supporter for the ankle Sn can contribute to the enhancement of durability. Furthermore, the tubular cover portion 2 is fitted to the user, and thus the load addition pattern portion P is also simultaneously fitted to the fixed position of the user. Hence, each time the supporter for the ankle Sn is used, complicated fitting and removing operations are not needed, and thus handling and usability are excellent, with the result that customer convenience can be enhanced. Moreover, it is possible to acquire comfort when the supporter for the ankle Sn is used. Specifically, since an uncomfortable feeling when the supporter for the ankle Sn is fitted is reduced, and the supporter for the ankle Sn is light-weight, it is possible to obtain a natural feeling of use, and it is easy to walk in a state where the supporter for the ankle Sn is fitted, with the result that safety is enhanced. In other words, it is possible to obtain these basic effects.

Although the preferred embodiments (the first to third embodiments) are described in detail above, the present invention is not limited to the embodiments described above, and changes, addition and deletion can be arbitrarily performed on the detailed configurations, shapes, materials, numbers, methods and the like without departing from the spirit of the present invention.

For example, although as the supporters 1, the sock Ss, the supporter for a knee Sk and the supporter for an ankle Sn are illustrated, the other supporters 1 include various types of supporters which can be fitted to a leg and various types of supporters which can be fitted to a hand and an arm and which can be made to function in the same manner. On the other hand, although for the manufacturing of the supporters 1, the method is illustrated in which the tubular cover portion 2 is fitted to the outer circumferential surface 11f of the cylindrical platen portion 11 and in which while the cylindrical platen portion 11 is being rotated, the load addition pattern portion P using the silicone rubber material Rc is subjected to screen printing, the present invention is not necessarily limited to this printing method (coating method), and other printing methods (coating methods) such as roller printing may be used. As long as the load addition pattern portion P can achieve the same actions (functions) as the supporters 1 according to the present embodiment, the load addition pattern portion P can be practiced with various shapes and designs. Furthermore, although as the mesh-shaped portion Pam, the honeycomb shape Pamh is illustrated, there is no limitation on mesh shapes based on various types of shapes, sizes and numbers. The load addition pattern portion P may be provided on the front surface (outer surface) of the tubular cover portion 2 or may be provided on the back surface (inner surface). Although as the elastic robber material R, the silicone rubber material Rc is used, various types of elastic rubber materials R such as latex rubber materials, acrylic resin, materials, polyurethane resin materials and synthetic materials can be used according to purposes. Hence, the conception of the elastic rubber material includes elastic resin materials.

INDUSTRIAL APPLICABILITY

The supporters (and the methods of manufacturing them) according to the present invention can be utilized for various types of supporters such as supporters for a leg and supporters for an arm that at least partially include a tubular cover portion which covers a part of a human body and which elastically expands and contracts.

The invention claimed is:
1. A supporter comprising:
a tubular cover is configured to cover a knee of a human body, said tubular cover is configured to elastically expand and contract, and
four load addition patterns printed on intended fixed positions on an outer surface of the tubular cover with a silicone rubber material, said four load addition patterns being a mesh formed in a honeycomb shape,
said four load addition patterns being adhered to the intended fixed positions on the outer surface of the tubular cover in a circumferential direction and configured to apply a load of a predetermined magnitude to the knee of the human body when the knee of the human body to which the tubular cover is fitted when the supporter is being worn is moved,
wherein the four load addition patterns include parts of adjacent portions of adjacent load addition patterns that are unitarily connected to each other and further include a ring configured to surround a protruding portion of the knee of the human body, and the four load addition patterns include a middle portion that is connected to and is continuously formed with a top portion, a bottom portion, a left portion and a right portion of said ring, each of the four load addition patterns is concave in a direction away from the ring and the middle portion is adapted to apply the load of the predetermined magnitude to the knee of the human body when the knee of the human body to which the tubular cover is fitted when the supporter is being worn is moved.

* * * * *